United States Patent
Li et al.

(10) Patent No.: US 10,449,313 B2
(45) Date of Patent: Oct. 22, 2019

(54) ULTRASOUND SCANNING APPARATUS, BREATHING MACHINE, MEDICAL SYSTEM AND RELATED METHOD

(71) Applicant: SHENZHEN MINDRAY BIO-MEDICAL ELECTRONICS CO., LTD., Shenzhen (CN)

(72) Inventors: Yong Li, Shenzhen (CN); Shuo Liu, Shenzhen (CN); Haibo Song, Shenzhen (CN); Yunxia Zuo, Shenzhen (CN); Jin Liu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 863 days.

(21) Appl. No.: 15/016,832

(22) Filed: Feb. 5, 2016

(65) Prior Publication Data
US 2016/0235931 A1    Aug. 18, 2016

Related U.S. Application Data

(63) Continuation of application No. PCT/CN2014/074414, filed on Mar. 31, 2014.

(30) Foreign Application Priority Data

Aug. 12, 2013  (CN) .......................... 2013 1 0350186

(51) Int. Cl.
*A61M 16/00* (2006.01)
*A61B 8/00* (2006.01)
(Continued)

(52) U.S. Cl.
CPC ......... *A61M 16/0069* (2014.02); *A61B 8/065* (2013.01); *A61B 8/0883* (2013.01);
(Continued)

(58) Field of Classification Search
CPC ... A61B 8/4416; A61B 8/5269; A61B 8/5276; A61B 8/543; A61B 8/06; A61B 8/065;
(Continued)

(56) References Cited

U.S. PATENT DOCUMENTS

2004/0092815 A1 * 5/2004 Schweikard ............. A61B 6/12
600/425
2005/0056283 A1 * 3/2005 Levi .................... A61M 16/021
128/204.21
(Continued)

FOREIGN PATENT DOCUMENTS

CN  1607016 A  4/2005
CN  101244304 A  8/2008
(Continued)

*Primary Examiner* — Joseph D. Boecker
(74) *Attorney, Agent, or Firm* — Kory D. Christensen

(57) ABSTRACT

An ultrasound scanning apparatus, a breathing machine, a medical system and a related method. The ultrasound scanning apparatus comprises an ultrasound scanning unit, an ultrasound controller for controlling the operation of the ultrasound scanning unit, detecting the operation state of the ultrasound scanning unit, generating a first enable signal when detecting that the operation state of the ultrasound scanning unit is transferred from an operating state to a nonoperating state and generating a second enable signal when detecting that the operation state of the ultrasound scanning unit is transferred from the nonoperating state to the operating state, and an enable output end for transmitting the first enable signal or the second enable signal to the breathing machine to control the running of the breathing machine.

9 Claims, 7 Drawing Sheets

(51) Int. Cl.
  *A61B 8/06* (2006.01)
  *A61B 8/08* (2006.01)
  *A61M 16/20* (2006.01)
  *A61M 16/10* (2006.01)
  *A61M 16/16* (2006.01)

(52) U.S. Cl.
  CPC .............. *A61B 8/5223* (2013.01); *A61B 8/54* (2013.01); *A61B 8/543* (2013.01); *A61M 16/021* (2017.08); *A61B 8/06* (2013.01); *A61B 8/4416* (2013.01); *A61B 8/463* (2013.01); *A61B 8/56* (2013.01); *A61M 16/1045* (2013.01); *A61M 16/1055* (2013.01); *A61M 16/16* (2013.01); *A61M 2205/058* (2013.01); *A61M 2205/3375* (2013.01)

(58) Field of Classification Search
  CPC ..... A61B 8/0858; A61B 8/0866; A61B 8/461; A61B 8/463; A61B 8/467; A61B 8/5223; A61B 8/54; A61B 8/56; A61M 16/00; A61M 16/0057; A61M 16/0066; A61M 16/0069; A61M 16/021; A61M 16/022; A61M 16/024; A61M 16/10; A61M 16/12; A61M 37/0092; A61M 2205/3375
  See application file for complete search history.

(56) References Cited

U.S. PATENT DOCUMENTS

| | | | |
|---|---|---|---|
| 2005/0085715 A1* | 4/2005 | Dukesherer | A61B 5/06 600/424 |
| 2005/0288585 A1* | 12/2005 | Zamboglu | A61B 5/0456 600/438 |
| 2006/0241461 A1* | 10/2006 | White | A61B 8/06 600/454 |
| 2009/0326389 A1* | 12/2009 | Ralfs | A61B 5/0205 600/485 |
| 2011/0144494 A1* | 6/2011 | Mehi | B06B 1/0622 600/441 |
| 2013/0274590 A1* | 10/2013 | Auboiroux | A61N 7/02 600/411 |
| 2017/0011509 A1* | 1/2017 | Ryu | G06T 7/70 |

FOREIGN PATENT DOCUMENTS

| | | |
|---|---|---|
| CN | 103126718 A | 6/2013 |
| JP | 2010005322 A | 1/2010 |

\* cited by examiner

ULTRASOUND SCANNING APPARATUS, BREATHING MACHINE, MEDICAL SYSTEM AND RELATED METHOD

FIELD OF THE INVENTION

The present disclosure relates to medical equipment and, more particularly, relates to an ultrasound scanning device, a ventilator, a medical system having the ultrasound scanning device and the ventilator, and a related method.

BACKGROUND OF THE INVENTION

An ultrasound scanning device is a convenient and non-invasive choice for cardiac monitoring, and is extensively applied in ICUs (Intensive Care Units), operating rooms, and occasions such as when moving a patient, due to its capacity to detect the movement information and structure of tissues and organs. The ultrasound scanning device can be used to continuously monitor real-time parameters of the patient's heart movements for a long period of time. The real-time parameters are hemodynamic parameters such as ejection fraction, ventricular volume, and blood flow rate. When in use the same cardiac section is scanned repeatedly, such that stable and consistent diagnostic parameters from the same cardiac section are acquired.

When the patient cannot breath on his own, such as when completely unconscious or under general anesthesia, a ventilator is required to perform respiratory ventilation on the patient. Respiratory assistance is one of the key means to rescue emergency or critical patients. Therefore, the ventilator is indispensable in clinical care. The breathing machine is more and more widely applied in fields of first aid, anesthesia, intensive care, and respiratory therapy. The ventilator can replace, control or change the normal physiological respiration of a person, increasing pulmonary ventilation volume, improving respiratory function, alleviating respiration consumption, and saving a cardiac reserve capability.

However, in practical clinical applications, because an increase in lung capacity is caused by mechanical ventilation, the lung tissue moves toward the heart and causes the position of the heart to change. The scanning region of the heart by the conventional ultrasound scanning device is constant. Once the position of the heart is changed, it is equivalent to that the ultrasound scanning device scanning different regions at different times and even the region outside the heart is scanned. This interferes with the stability and accuracy of images captured by the ultrasound scanning device.

FIGS. 1 and 2 show sectional views along a ventricular short axis. The white line segments in FIGS. 1 and 2 indicate the same reference position, and it is apparent the heart moves from side to side due to an air feed of the ventilator causes the section scanned by the scanning line to be changed accordingly. Therefore, the data acquired by the scanning line is not based upon the same section, such that the ultrasound scanning result loses its meaning. Therefore, in existing clinical conditions, the scanning of the ultrasound scanning device is generally controlled by the doctor via perusal, and the stability and the accuracy of the scanning result is inadequate.

SUMMARY OF THE INVENTION

Accordingly, it is necessary to provide an ultrasound scanning device, a ventilator, a medical system having the ultrasound scanning device and the ventilator, and a related method which can ensure better stability and accuracy of an ultrasound scanning result.

An ultrasound scanning device includes: an ultrasound scanning unit; an ultrasound controller configured to control the ultrasound scanning unit to work and to detect a working state of the ultrasound scanning unit, wherein the ultrasound controller is configured to generate a first enable signal when detecting the working state of the ultrasound scanning unit is switched to a nonworking state, and the ultrasound controller is configured to generate a second enable signal when detecting the nonworking state of the ultrasound scanning unit is switched to the working state; and an enable output end configured to transmit the first enable signal or the second enable signal to a ventilator to control an operation of the ventilator.

A ventilator corresponding to the foregoing ultrasound scanning device includes: a pneumatic unit configured to generate respiration air flow; an enable input end configured to receive a first enable signal or a second enable signal from an ultrasound scanning device, the first enable signal or the second enable signal obtained according to a working state of the ultrasound scanning device; and a breathing controller configured to trigger the pneumatic unit to work according to the first enable signal, or trigger the pneumatic unit to stop working according to the second enable signal.

A control method of a ventilator which includes a pneumatic unit configured to generate a respiration air flow, the method including: receiving a first enable signal and a second enable signal from an ultrasound scanning device, wherein the first enable signal is generated when an ultrasound controller of the ultrasound scanning device detects a working state of an ultrasound scanning unit is switched to a nonworking state, and the second enable signal is generated when the ultrasound controller of the ultrasound scanning device detects a nonworking state of the ultrasound scanning unit is switched to the working state; and triggering the pneumatic unit to work according to the first enable signal, or triggering the pneumatic unit to stop working according to the second enable signal.

A first medical device includes: an above described ultrasound scanning device and a ventilator, wherein the enable output end of the ultrasound scanning device is connected to the enable input end.

An ultrasound scanning device includes: an ultrasound scanning unit; a periodic input end configured to receive a ventilation periodic signal from a ventilator; and an ultrasound controller configured to analyze the ventilation periodic signal, and to generate an ultrasound scanning time sequence according to an analytical result; and the ultrasound scanning unit performs an ultrasound scanning according to the ultrasound scanning time sequence.

A ventilator corresponding to above described ultrasound scanning device, the ventilator including: a pneumatic unit configured to generate a respiration air flow; and a periodic output end configured to transmit a ventilation periodic signal of the pneumatic unit to an ultrasound scanning device.

A scanning method of an ultrasound scanning device includes: receiving a ventilation periodic signal from a ventilator; analyzing the ventilation periodic signal and generating an ultrasound scanning time sequence according to an analytical result; and performing an ultrasound scanning according to the ultrasound scanning time sequence.

A second medical device includes: an above described ultrasound scanning device and ventilator, wherein a periodic input end of an ultrasound scanning device is connected to a periodic output end of the ventilator.

A medical system includes: a first medical device; a second medical device; and a medical processor, wherein the medical processor is configured to trigger the first medical device or the second medical device to work according to an inputted selection instruction, the selection instruction including an instruction to select the first medical device to work and an instruction to select the second medical device to work.

In the above device, the enable signal of the ultrasound scanning device is transmitted to the ventilator, so as to provide a reference for running subsequent operation of the ventilator. Thus, it is possible to determine mechanical ventilation is provided during ultrasound scanning.

BRIEF DESCRIPTION OF THE DRAWINGS

To illustrate the embodiments of the present disclosure more clearly, the accompanying drawings are included. The accompanying drawings only show some embodiments of the present disclosure, and persons of ordinary skill in the art can derive other embodiments from the accompanying drawings.

DETAILED DESCRIPTION OF THE EMBODIMENTS

Specific details for fully understanding various embodiments and being implemented by one skilled in the art are provided in the following. However, one skilled in the art can understand that the invention may be implemented without these details. In some embodiments, above well-known structures and the functions are not specifically shown or described, in order to avoid unnecessary confusion of the description of the embodiments.

Unless clearly defined through the text, the terms "comprise," "contain" and so on throughout the description and the claims shall be interpreted to be inclusive and not to be exclusive or exhaustive, i.e., "including but not limited to." In the specific description, plural or singular terms respectively include plural objects or singular objects. In addition, the terms "herein," "above" and "following" and similar terms used in the application refer to the whole application, not to any specific part.

Figure 1:
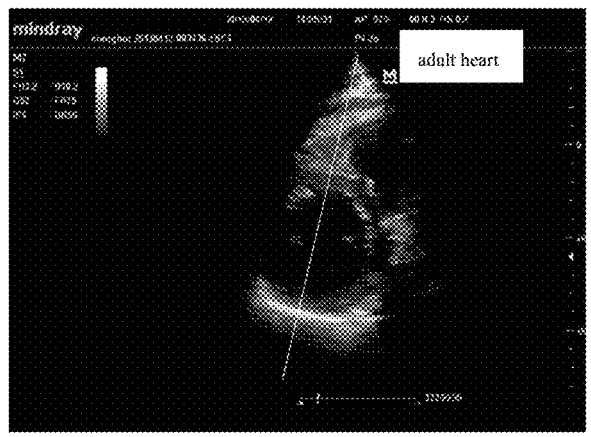
FIGS. 1 and 2 are schematic sectional views along a same ventricular short axis illustrating interference under a mechanical ventilation.
Figure 2:
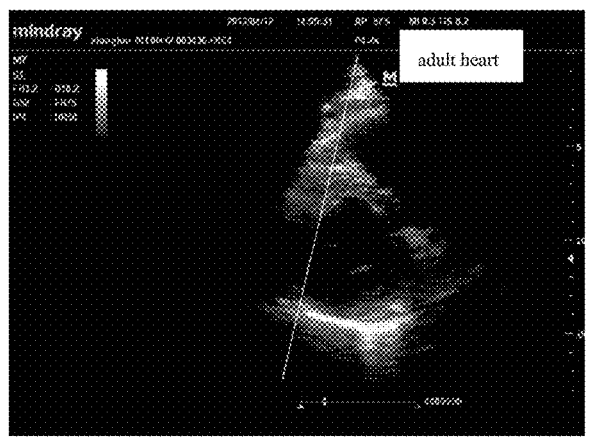
Figure 3:
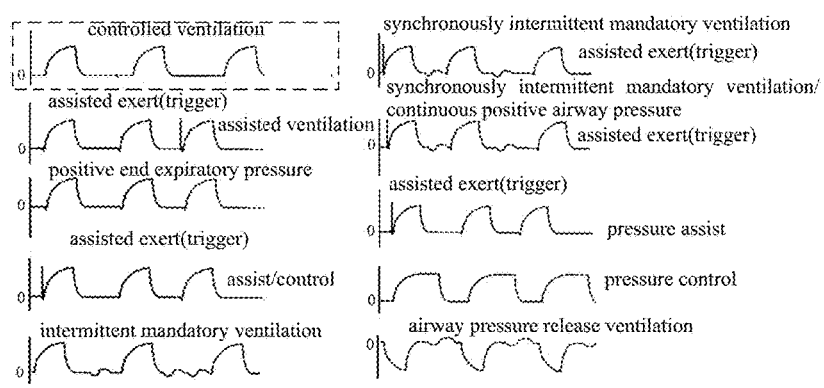
FIG. 3 is a schematic view of a pressure curve in a commonly used ventilation mode.

When autonomous respiration is performed, the aspiratory action (mainly the diaphragm's movement) generates an intra-thoracic negative pressure, the lung is expanded, and pulmonary alveoli and airway negative pressure emerge, thereby generating a pressure difference between the airway opening and the pulmonary alveoli to accomplish the inspiration. When the inspiration is accomplished, the thorax and the lung elastically recoil, and generate an opposite pressure difference to accomplish the expiration. Therefore, normal respiration is: an organism generates an active negative pressure difference between the pulmonary alveoli and the airway opening by breathing action to accomplish the inspiration, and after the inspiration, the thorax and the lung elastically recoil and generate a passive positive pressure difference between the pulmonary alveoli and the airway opening to accomplish the expiration, thereby meeting a requirement of physiological ventilation. However, ventilator ventilation is: an external machine drives to generate a positive pressure difference between the pulmonary alveoli and the airway opening to accomplish the inspiration, and after the removal of external machine pressure, the thorax and the lung elastically recoil and generate a passive positive pressure difference between the pulmonary alveoli and the airway opening to accomplish the expiration, that is "the passive positive pressure difference" exists in the respiratory cycle to accomplish the respiration. The positive pressure difference increases the lung capacity, causing the lung tissue to move toward the heart, thoracic wall and diaphragm. As shown in FIG. 3, a pressure curve of commonly used ventilation mode includes controlled ventilation, assisted ventilation, positive end expiratory pressure, assist/control ventilation, and synchronously intermittent mandatory ventilation/continuous positive airway pressure, and so on. For the patient without autonomous respiration ability, complete mechanical control ventilation modes such as VCV (volume control ventilation) or PCV (pressure control ventilation) are required. At the time, the working cycle of the ventilator is a curve as shown in the dashed box, i.e., the respiration cycle of the patient is wholly controlled by the ventilator. For the patient having some autonomous respiration ability, intermittent mandatory ventilation such as SIMV-VC (synchronized intermittent mandatory ventilation of volume control) or SIMV-PC (synchronized intermittent mandatory ventilation of pressure control) can be used to control the ventilation mode, to strengthen patient-ventilator coordination. For a patient having strong autonomous respiration ability, the PS (pressure assist) ventilation mode can be selected, i.e., the patient is merely provided with ventilation assistance. It can be verified by analyzing, in the situation of completely passive breathing, the ventilator mechanism causes the position of the heart to be changed, and the displacement cycle of the heart is synchronized with the mechanical ventilation cycle.

Based upon the above analysis, the present disclosure provides a solution to exclude the ventilator's mechanical ventilation interference during the ultrasound scanning, and the solution suppresses interference caused by a cardiac movement in data collection, in which the cardiac movement is caused by mechanical ventilation, thereby avoiding the complexity of post-data processing, and, at the same time, achieving a stable and accurate ultrasound scanning result. The present disclosure is illustrated in the following embodiments with reference to accompanying drawings.

Figure 4:
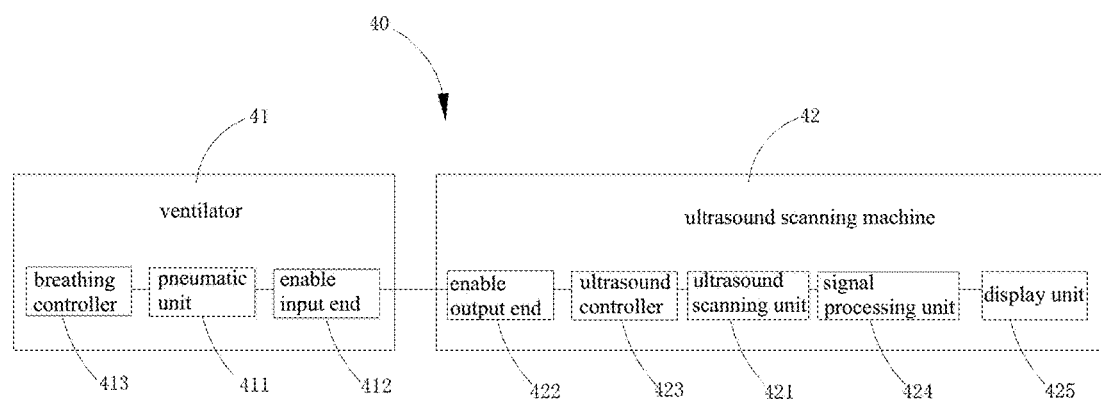
FIG. 4 is a structural view of a medical device according to an embodiment.

As shown in FIG. 4, a medical device 40 according to an embodiment includes a ventilator 41 and an ultrasound scanning device 42.

The ventilator 41 can be connected to one or more appropriate air source (not shown). The air source can be an external or internal driving source. The air is adjusted into a respiration gas in a pneumatic unit 411, which is configured to generate a respiration gas flow. The ventilator 41 can further include a valve configured to control pressure and flux of the respiration gas. The respiration gas is then introduced to the patient by connecting mechanisms such as an air suction pipe, a breathing mask, and an exhale pipe. The pneumatic unit 411 is controlled by a breathing controller 413, and the breathing controller 413 can provide control for commonly used ventilation modes, such as a switch of the ventilation modes. The ventilator 41 can further include other standardized components, such as a humidifier, a dehumidifier, a bacterial filter, and a humidity and heat exchanger.

The above described ventilator 41 has a function to control the working of the ventilator 41 according to a signal of the ultrasound scanning device 42. Specifically, the ventilator 41 receives a first enable signal or a second enable signal from the ultrasound scanning device 42 by an enable input end 412; therefore, the breathing controller 413 triggers the pneumatic unit 411 to work according to the received first enable signal, or triggers the pneumatic unit 411 to stop working according to the received second enable signal. The enable input end 412 and the breathing controller 413 can be an additionally added port and control component on the ventilator 41, or can be a blank port by currently assigning a new definition to the blank port, and also can be reused on the existing port and control component without affecting the operation of the original function.

In the ultrasound scanning device 42, an ultrasound scanning unit 421 is configured to transmit an ultrasonic wave to and receive an ultrasonic wave from the portion to be detected, to enable the ultrasound scanning device 42 to scan and detect human organs. A signal processing unit 424 processes the ultrasound echo signal obtained by the ultrasound scanning unit 421, and transmits the ultrasound echo signal into an image and corresponding physiological parameters, for example, hemodynamic parameters such as blood flow rate, ventricular volume and ejection fraction. A display unit 425 is configured to display the image and corresponding physiological parameters which are obtained by the signal processing unit 424. The ultrasound scanning unit 421, the signal processing unit 424 and the display unit 425 can be realized by adopting corresponding functional modules in the commonly used ultrasound scanning device 42.

Further, in the embodiment, the ultrasound scanning device 42 further includes an enable output end 422 and an ultrasound controller 423. The ultrasound controller 423 controls the ultrasound scanning unit 421 to work and detects the working state of the ultrasound scanning unit 421. When the ultrasound controller 423 detects that the working state of the ultrasound scanning unit 421 is switched to a nonworking state, a first enable signal is generated; when the ultrasound controller 423 detects that the nonworking state of the ultrasound scanning unit 421 is switched to a working state, a second enable signal is generated. The enable output end 422 can transmit the first enable signal or the second enable signal out, such as to the ventilator 41. In other words, when the ultrasound controller 423 detects that the ultrasound scanning unit 421 is in a working state, the second enable signal is transmitted to the ventilator 41 by the enable output end 422, and the breathing controller 413 controls the pneumatic unit 411 to stop mechanical ventilation. When the ultrasound controller 423 detects that the ultrasound scanning unit 421 has stopped the scanning, the first enable signal is transmitted to the ventilator 41 by the enable output end 422, and the breathing controller 413 controls the pneumatic unit 411 to resume mechanical ventilation. The enable output end 422 and the ultrasound controller 423 can be an additionally added port and control component on the original ultrasound equipment, or can be a blank port by currently assigning a new definition to the blank port, and also can be reused on the existing port and control component without affecting the operation of the original function.

The enable input end 412 of the ventilator 41 and the enable output end 422 of the ultrasound scanning device 42 are electrically connected, the electrical path thereof can be in various ways. The most direct way is an electrical connection which can be a wired connection, and another way can be wireless coupling. The enable input end 412 of the ventilator 41 and the enable output end 422 of the ultrasound scanning device 42 can be configured in different ways. For example, both are recessed sockets, and a conductive wire having plugs on opposite ends is adaptively inserted into the recessed sockets. Or, the enable input end 412 of the ventilator 41 is a conductive wire with a plug at an end. The other end of the conductive wire is connected to the breathing controller 413, the enable output end 422 of the ultrasound scanning device 42 is a socket, and the conductive wire with a plug is inserted into the socket, to realize an interconnection between the ventilator 41 and the ultrasound scanning device 42. Or, the enable output end 422 of the ultrasound scanning device 42 is a conductive wire with a plug at an end. The other end of the conductive wire is connected to the ultrasound controller 423 of the ultrasound scanning device 42, the enable input end 412 of the ventilator 41 is a socket, the conductive wire with a plug is inserted into the socket, to realize an interconnection between the ventilator 41 and the ultrasound scanning device 42. Specifically, during use, after the ventilator 41 is interconnected to the ultrasound scanning device 42, the enable output end 422 of the ultrasound scanning device 42 can actively transmit the first enable signal or the second enable signal to the ventilator 41, and the enable output end 422 can also passively transmit the enable signals to the ventilator 41, which can be determined by changing according to a specific requirement.

Generally, the standby time of the ventilator 41 has a constant upper limit; it is called the ventilator stop upper limit. When the ultrasound controller 423 detects the continuous working time of the ultrasound scanning unit 421 has reached the ventilator stop upper limit, the ultrasound controller 423 controls the ultrasound scanning unit 421 stopping scanning, and outputs the first enable signal to the ventilator 41. The ultrasound controller 423 controls the pneumatic unit 411 to resume mechanical ventilation. It can be configured that when the pause time of the ventilator 41 exceeds a preset value, the ventilation is resumed. The preset value is an appropriate value within the ventilator stop upper limit.

Figure 5:
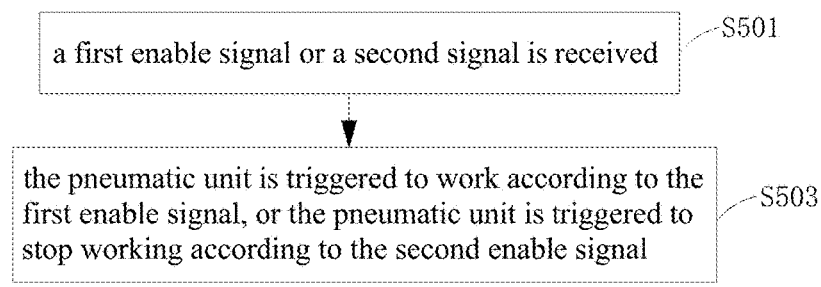
FIG. 5 is a schematic view of a working flow of a control method of a ventilator according to an embodiment.

A control method of a ventilator according to an embodiment, as shown in FIG. 5, the method including the following steps:

In step S501, a first enable signal and a second enable signal are received from the ultrasound scanning device, the first enable signal is generated when the ultrasound controller of the ultrasound scanning device detecting the working state of the ultrasound scanning unit is switched to a nonworking state, and the second enable signal is generated when the ultrasound controller of the ultrasound scanning device detecting the nonworking state of the ultrasound scanning unit is switched to the working state. In addition, the standby time of the ventilator generally has a constant upper limit, i.e., the ventilator stop upper limit; therefore, the first enable signal can also be generated when a continuous working time of the ultrasound scanning device reaching ventilator stop upper limit is detected by the ultrasound controller.

The ventilator 41 and the ultrasound scanning device 42 establish a connection therebetween for communication via the enable output end 422 and the enable input end 412, and the above description about the medical device can be referred to for the communication connection way. From the perspective of the ultrasound scanning device 42, when the ultrasound controller 423 detects that the ultrasound scanning unit 421 is in a working state, the second enable signal is transmitted to the ventilator 41 by the enable output end 422. When the ultrasound controller 423 detects that the ultrasound scanning unit 421 has stopped the scanning, the first enable signal is transmitted to the ventilator 41 by the enable output end 422.

In step S503, the pneumatic unit is triggered to work according to the first enable signal, or the pneumatic unit is triggered to stop working according to the second enable signal.

From the perspective of the ventilator 41, when the enable input end 412 of the ventilator 41 receives the first enable signal, the breathing controller 413 controls the pneumatic unit 411 to resume the mechanical ventilation. When the enable input end 412 of the ventilator 41 receives the second enable signal, the breathing controller 413 controls the pneumatic unit 411 to stop mechanical ventilation.

Although from the perspective of the ultrasound scanning device 42 the ultrasound controller 423 is required to generate the first enable signal when the continuous working time of the ultrasound scanning unit 421 has reached the ventilator stop upper limit, from the perspective of the ventilator 41 it can be configured that when the pause time of the ventilator 41 exceeds a preset value, the ventilation is resumed, and the preset value is an appropriate value within the ventilator stop upper limit.

The above description of the medical device can be referred to for specific realization of each step of the above method and is not described herein.

Figure 6:
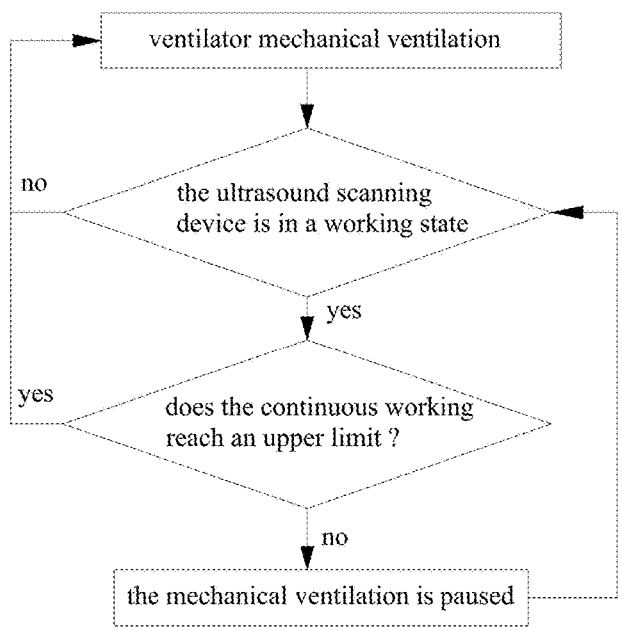
FIG. 6 is a schematic view of a working flow of the medical device of FIG. 4.

In FIG. 6, a schematic view of a working flow of a medical device is shown according to one embodiment wherein the ultrasound scanning device 42 transmits the enable signal to the ventilator 41 when the ultrasound scanning device 42 is in a working state and the ventilator 41 pauses the mechanical ventilation; therefore, it can ensure that the heart is in the same position every time the ultrasound scanning device 42 scans.

Figure 7:
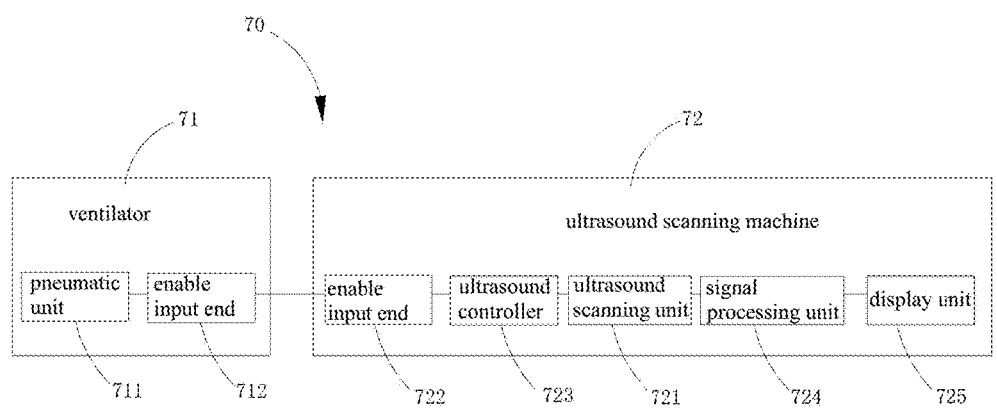
FIG. 7 is a structural view of a medical device according to an embodiment.

As shown in FIG. 7, in one embodiment, a medical device 70 includes a ventilator 71 and an ultrasound scanning device 72.

The ventilator 71 can be connected to one or more appropriate air source (not shown). The air source can be an external or internal driving source. The air is adjusted into a respiration gas in a pneumatic unit 711, which is configured to generate a respiration gas flow. The pneumatic unit 711 can include a valve configured to control a pressure and a flux of the respiration gas. The respiration gas is then introduced to the patient by connecting mechanisms such as an air suction pipe, a breathing mask, and an exhale pipe. The ventilator 71 can further include other standardized components, such as a humidifier, a dehumidifier, a bacterial filter, and a humidity and heat exchanger.

Figure 8:
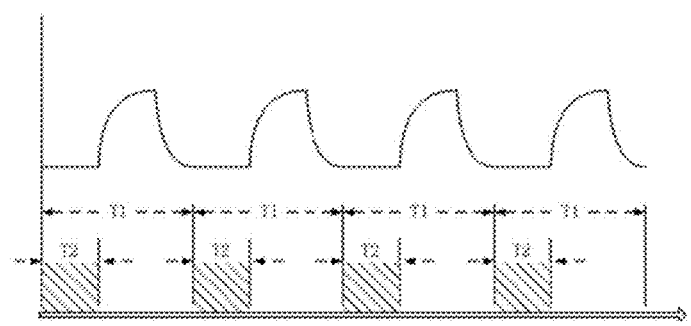
FIG. 8 is a schematic view of a pressure curve of the ventilator of the medical device of FIG. 7 in a controlled ventilation mode.

The ventilator 71 transmits the ventilation periodic signal of the pneumatic unit 711 to an ultrasound scanning device 72 via the periodic output end 712. The periodic output end 712 can be an additionally added port on the ventilator 71, or can be a blank port by currently assigning a new definition to the blank port, and also can be reused on the existing port and control component without affecting the operation of the original function. FIG. 8 is a schematic view of a pressure curve when the ventilator 41 is in a controlled ventilation mode. The horizontal axis represents a timeline, and it can be seen that the mechanical ventilation period of the pneumatic unit 711 is T1. Herein, the periodic signal can indicate the periodic signal of a constant period, and can also be a periodic signal of a variable period, if only the control signal controls the ventilator 41 to ventilation, the control signal can be treated as the ventilation periodic signal.

Also as similar to embodiment 1, in the ultrasound scanning device 72, an ultrasound scanning unit 721 is configured to transmit an ultrasonic wave to and receive an ultrasonic wave from the portion to be detected, to enable the ultrasound scanning device 72 to scan and detect the human organs. A signal processing unit 724 processes the ultrasound echo signal obtained by the ultrasound scanning unit 721, and transmits the ultrasound echo signal into an image and corresponding physiological parameters, for example, the hemodynamic parameters such as blood flow rate, ventricular volume and ejection fraction. A display unit 725 is configured to display the image and corresponding physiological parameters which are obtained by the signal processing unit 724. The ultrasound scanning unit 721, the signal processing unit 724 and the display unit 725 can be realized by adopting corresponding functional modules in the commonly used ultrasound scanning device 72.

In addition to the ultrasound scanning unit 721, the signal processing unit 724, and the display unit 725, the ultrasound scanning device 72 according to the embodiment further includes a periodic input end 722 and an ultrasound controller 723. The periodic input end 722 is configured to receive a ventilation periodic signal form the ventilator 71. The ultrasound controller 723 is configured to analyze the ventilation periodic signal, generates a scanning time sequence according to an analytical result, and controls the ultrasound scanning unit 721 to perform an ultrasound scanning according to the generated ultrasonic scanning time sequence. The periodic input end 722 and the ultrasound controller 723 can be an additionally added port and control component on the ultrasound scanning device 72, or can be a blank port by currently assigning a new definition to the blank port, and also can be reused on the existing port and control component without affecting the operation of the original function.

In order to better exclude the mechanical ventilation interference of the ventilator, in the generated ultrasonic scanning time sequence, the scanning period of the ultrasound scanning unit 721 should be synchronized with the ventilation periodic signal. The starting point of each scanning of the ultrasound scanning unit 721 falls always on the position which is a starting point of each periodic signal plus a first preset time value. The end point of each scanning falls always on the position which is a starting point of each periodic signal plus a second preset time value. The first preset time value can be zero, and can also be another positive number. For each ventilation period, the result of the second preset time value plus the starting point of the ventilation period still falls within the period, i.e., the starting point and the end point of each scanning are positioned in one ventilation period. That is, referring to FIG. 8, the ventilator 71 transmits the periodic signal of the mechanical ventilation to the ultrasound scanning device 72, and the periodic signal can be interpreted as a time sequence, i.e., the ventilation periodic signal includes a periodic information T1. The ultrasound controller 723 outputs an ultrasound scanning time sequence according to the inputted ventilation periodic signal, i.e., the ultrasound scanning time period T2. The time period T2 falls within a constant time period within T1, for example, T2 can start from the starting point of T1 to the starting point of T1 plus two seconds, or can start from the starting point of T1 plus three seconds to the starting point of T1 plus five seconds, and so on. Finally, the ultrasound scanning unit 721 performs an ultrasound scanning according to a requirement and the time sequence generated by the ultrasound controller 723. In addition, T2 merely falls on a same position in each T1, and not always starts the starting point to the end point when the ventilator 71 stops supplying gas.

It should be understood that, in order to enable a communication between the ultrasound scanning device and the breathing device, the scanning device and the breathing device are required to perform a communication according to a previously agreed protocol. The ventilator packages the ventilation periodic signal and transmits it according to the protocol. The ultrasound scanning device receives and analyzes the packaged ventilation periodic signal according to the protocol. Communication related technology of the commonly used device can be referred to for realizing the specific communication protocol; it is not limited herein.

Similar to the above embodiment, the enable input end of the ventilator 71 and the enable output end of the ultrasound scanning device 72 are electrically connected, and the electrical path thereof can be in various ways. The most direct way is an electrical connection. The enable input end of the ventilator 71 and the enable output end of the ultrasound scanning device 72 can be in different types. For example, both are recessed sockets, and a conductive wire having plugs on opposite ends is adaptively inserted into the recessed sockets. Or, the enable input end of the ventilator 71 is a conductive wire with a plug at an end. The other end of the conductive wire is connected to the breathing controller of the ventilator 71, the enable output end of the ultrasound scanning device 72 is a socket, and the conductive wire with a plug is inserted into the socket, to realize an interconnection between the ventilator 71 and the ultrasound scanning device 72. Or, each of the enable output end of the ultrasound scanning device 72 and the enable input end of the ventilator 71 is a conductive wire with a plug at an end. The other end of the conductive wire is connected to the ultrasound controller of the ultrasound scanning device 72, the enable input end of the ventilator 71 is a socket, and the conductive wire with a plug is inserted into the socket, to realize an interconnection between the ventilator 71 and the ultrasound scanning device 72. During use, after the ventilator 71 is interconnected to the ultrasound scanning device 72, the enable output end of the ultrasound scanning device 72 can actively transmit the first enable signal or the second enable signal to the ventilator 71, and the enable output end can also passively transmit the enable signals to the ventilator 71. It can be determined by changing according to a specific requirement.

Figure 9:
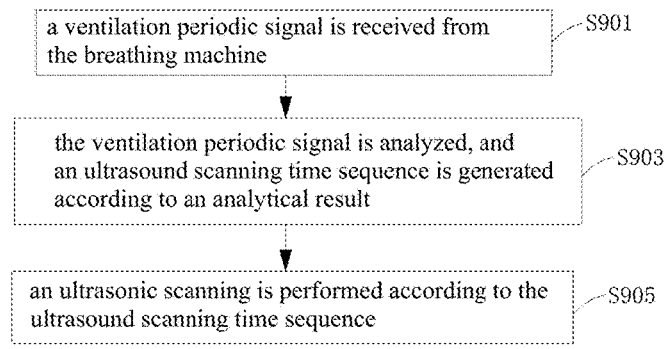
FIG. 9 is a schematic view of a working flow of a scanning method of an ultrasound scanning device according to an embodiment.

A scanning method of an ultrasound scanning device according to an embodiment is shown as FIG. 9 and includes steps as follows:

In step S901, a ventilation periodic signal is received from the ventilator.

The above described medical device can be referred to for the communication connection between the ventilator and the ultrasound scanning device. In order to enable a communication between the ultrasound scanning device and the breathing device, the scanning device and the breathing device are required to perform a communication according to a previously agreed protocol. The ventilator packages the ventilation periodic signal and transmits it according to the protocol. Communication related technology of the commonly used equipment can be referred to for realizing the specific communication protocol; it is not limited herein.

In step S903, the ventilation periodic signal is analyzed, and an ultrasound scanning time sequence is generated according to an analytical result.

The ultrasound scanning device receives and analyzes the ventilation periodic signal which is packaged by the ventilator according to the previously agreed protocol, and generates an ultrasound scanning time sequence according to an analytical result. In order to better suppress the mechanical ventilation interference of the ventilator, in the generated ultrasonic scanning time sequence, the scanning period of the ultrasound scanning unit should be synchronized with the ventilation periodic signal. That is to say, the starting point of each scanning of the ultrasound scanning unit falls always on the position which is a starting point of each periodic signal of the ventilator plus a first preset time value. The end point of each scanning falls always on the position which is a starting point of each ventilation periodic signal plus a second preset time value. The first preset time value can be zero, and can also be another positive number. For each ventilation period, the second preset time value plus the starting point of the ventilation period still falls within the ventilation period, i.e., the starting point and the end point of each scanning are positioned in one ventilation period; therefore, each T2 as shown in FIG. 8 falling on the constant position of each T1 can be ensured.

In step S905, the ultrasound scanning unit performs an ultrasound scanning according to the ultrasound scanning time sequence.

The foregoing description about the medical device can be referred to for the specific realization of each step of the above method, and is not described herein.

The medical device according to the embodiment transmits the mechanical ventilation periodic signal to the ultrasound scanning device, and enables the scanning interval of the ultrasound scanning device to be synchronized with the mechanical ventilation of the ventilator, thereby ensuring the heart is in the same position every time the ultrasound scanning device scans.

Figure 10:
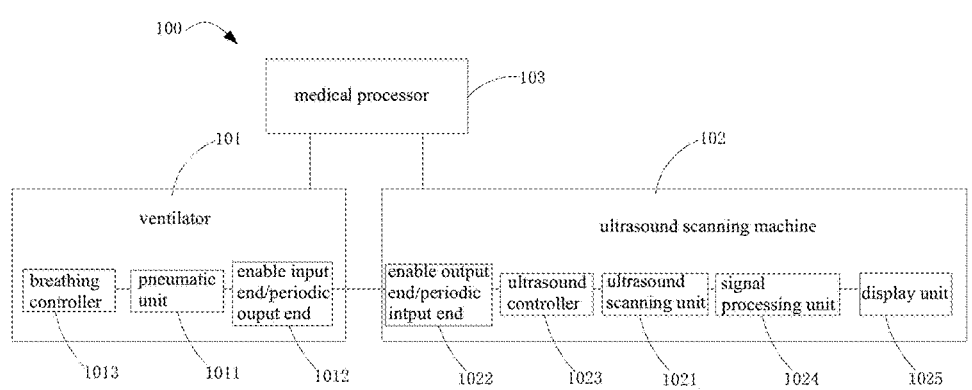
FIG. 10 is a block diagram of a medical system according to an embodiment.

As shown in FIG. 10, a medical system 100 according to one embodiment includes a medical processor 103, a ventilator 101, and an ultrasound scanning device 102. The ventilator 101 has functions of the ventilator mentioned in embodiments 1 and 2, the ultrasound scanning device 102 has functions of the ultrasound scanning device mentioned in embodiments 1 and 2, i.e., the medical system 100 provides a first medical device of "the ultrasound scanning device controlled ventilator" of the first embodiment and a second medical device of "the ventilator controlled ultrasound scanning device" of the second embodiment, and the medical processor 103 is configured to select the first medical device or the second medical device to work according to a selection instruction inputted by user. That is to say, the selection instruction includes the instruction to select the first medical device to work and the instruction to select the second medical device to work.

It can be understood that the medical system 100 according to the embodiment provides a user interaction interface, for example, providing window displaying selections or providing selective buttons. The selective buttons or the selective windows are expression modes of selection instructions; they can also be in other modes. For example, the ventilator 101 is provided with two ports: one port is configured to assist the enable input end, and the other port is configured to assist the periodic output end. At the same time, the ultrasound scanning device 102 is also provided with two ports, one port configured to assist the enable output end, the other port configured to assist the periodic input end, and when the enable input end is connected to the enable output end, it indicates that the user selects the first medical device of "the ultrasound scanning device controlled ventilator" provided above; likewise, when the periodic input end and the periodic output end are connected, it indicates that the user selects the second medical device of "the ventilator controlled ultrasound scanning device" provided by embodiment 2.

In one embodiment, by virtue of inputting the signal of the ventilator 101 into the ultrasound scanning device 102, the scanning interval of the ultrasound scanning device 102 is synchronized with the mechanical ventilation period of the ventilator 101. In another embodiment, by virtue of inputting the scanning signal of the ultrasound scanning device 102 into the ventilator 101, when the ultrasound scanning device 102 is in a working state, the ventilator 101 pauses the mechanical ventilation. Either way, it can ensure that the heart is in the same position every time the ultrasound scanning device 102 scans. In the data source, interference caused by heart movement, which is a result of the mechanical ventilation, is suppressed, avoiding the complexity of post-data processing, and, at the same time, achieving a stable and accurate ultrasound scanning result.

One skilled in the art can understand that all or part of the steps of various methods in the embodiments can be implemented by related hardware which is instructed by program. The program may be stored in a computer readable storage medium. The storage medium may include: a read-only memory, a random access memory, a magnetic disk or an optical disc.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. An ultrasound scanning device, comprising:
   an ultrasound scanning unit configured to operate in a scanning mode and a non-scanning mode;
   a communication interface configured to receive a ventilation periodic signal, the ventilation periodic signal including data corresponding to a pressure curve indicating mechanical ventilation pressures applied onto a patient;
   an ultrasound controller configured to analyze the received ventilation periodic signal and generate a scanning schedule of time intervals based on the analysis of the ventilation periodic signal;
   wherein the ultrasound controller controls the ultrasound scanning unit to operate in the scanning mode and the non-scanning mode during the time intervals scheduled in the scanning schedule;
   the scanning schedule comprises scanning periods corresponding to periods of time in which the ultrasound scanning unit is controlled by the ultrasound controller to scan a heart region in the scanning mode;
   each scanning period during which the ultrasound scanning unit scans the heart region corresponds to a time interval of the ventilation periodic signal during which the pressure curve is at about a minimum, wherein the pressure curve at about the minimum refers to a situation of stopping applying the mechanical ventilation to the patient.

2. The ultrasound scanning device of claim 1, wherein the scanning schedule further comprises non-scanning periods corresponding to periods of time in which the ultrasound scanning unit is scheduled to operate in the non-scanning mode, wherein each of the non-scanning periods start a second preset amount of time after each starting point of each period of the ventilation periodic signal.

3. The ultrasound scanning device according to claim 1, wherein the ultrasound controller is configured to analyze the ventilation periodic signal according to a protocol that is previously agreed upon by the ultrasound scanning device and a ventilator.

4. The ultrasound scanning device of claim 1, wherein the scanning schedule is periodic and synchronized with the ventilation periodic signal.

5. The ultrasound scanning device of claim 1, wherein each of the scanning periods start a first preset amount of time after each starting point of each period of the ventilation periodic signal, and each of the scanning periods ends a second preset amount of time after each starting point of each period of the ventilation periodic signal; the first preset amount of time is unequal to the second preset amount of time.

6. The ultrasound scanning device of claim 5, wherein each of the scanning periods starts and ends at the same position in each period of the ventilation periodic signal.

7. The ultrasound scanning device of claim 5, wherein each of the scanning periods starts and ends within one single period of the ventilation periodic signal.

8. The ultrasound scanning device of claim 1, wherein the scanning schedule further comprises non-scanning periods corresponding to periods of time in which the ultrasound scanning unit is scheduled to operate in the non-scanning mode; at least a portion of each non-scanning period corresponds to a time interval of the ventilation periodic signal during which the pressure curve is at a ramp-up or a ramp-down stage.

9. The ultrasound scanning device of claim 1, wherein the scanning schedule further comprises non-scanning periods corresponding to periods of time in which the ultrasound scanning unit is scheduled to operate in the non-scanning mode; each scanning period plus each non-scanning period is substantially equal to one period of the ventilation periodic signal.

* * * * *